United States Patent
Martin et al.

(10) Patent No.: US 10,321,868 B2
(45) Date of Patent: Jun. 18, 2019

(54) METHODS AND APPARATUS FOR CONSISTENT AND ACCURATE CERVICAL DILATION READINGS DURING LABOR AND DELIVERY

(71) Applicants: Eva Lea Martin, San Francisco, CA (US); Brandon Martin, San Francisco, CA (US)

(72) Inventors: Eva Lea Martin, San Francisco, CA (US); Brandon Martin, San Francisco, CA (US)

(*) Notice: Subject to any disclaimer, the term of this patent is extended or adjusted under 35 U.S.C. 154(b) by 213 days.

(21) Appl. No.: 14/856,472

(22) Filed: Sep. 16, 2015

(65) Prior Publication Data
US 2016/0270713 A1    Sep. 22, 2016

Related U.S. Application Data

(60) Provisional application No. 62/133,897, filed on Mar. 16, 2015.

(51) Int. Cl.
*A61B 5/00* (2006.01)
*A61B 5/107* (2006.01)
(Continued)

(52) U.S. Cl.
CPC ............ *A61B 5/435* (2013.01); *A61B 5/1076* (2013.01); *A61B 5/6806* (2013.01);
(Continued)

(58) Field of Classification Search
CPC .... A61B 5/435; A61B 5/1076; G01B 3/1005; G01B 3/1007; G01B 3/1084; G01B 3/46
See application file for complete search history.

(56) References Cited

U.S. PATENT DOCUMENTS 4,245,656 A    1/1981   Farr et al.
4,611,603 A    9/1986   Kelso et al.
(Continued)

OTHER PUBLICATIONS

International Search Report and Written Opinion in PCT Application No. PCT/US2015/050521 dated Dec. 14, 2015.

*Primary Examiner* — Devin B Henson
(74) *Attorney, Agent, or Firm* — Michael R. Shevlin

(57) ABSTRACT

A cervical dilation reading apparatus and method of use to accurately and precisely determine cervical dilation measurements during labor and delivery. The apparatus includes a measuring device having a length with a first end and a second end, a fixed attachment configured to couple with a first finger and fixedly engage the first end of the measuring device, and a slidable attachment configured to couple with a second finger and slidably engage the measuring device along the length between the first and second ends. The method includes providing a cervical dilation reading apparatus, inserting the first and second fingers into the vaginal introitus and locating the cervix and cervical os, placing the first finger on a first side of the cervical os and extending the second finger away from the first finger to a second side, opposite the first side, of the cervical os, thereby extending the length of the measuring device between the first and second fingers to a substantially extended state, removing the first and second fingers, and determining a diameter of the cervical os by the length of the measuring device in the substantially extended state between the fixed attachment and slidable attachment.

7 Claims, 4 Drawing Sheets

(51) Int. Cl.
*G01B 3/10* (2006.01)
*G01B 3/46* (2006.01)

(52) U.S. Cl.
CPC .......... *G01B 3/1005* (2013.01); *G01B 3/1084* (2013.01); *G01B 3/46* (2013.01)

(56) References Cited

U.S. PATENT DOCUMENTS

| | | | |
|---|---|---|---|
| 6,066,104 A | 5/2000 | Dao et al. | |
| 6,450,977 B1* | 9/2002 | Baxter-Jones | A61B 5/1076 600/591 |
| 2007/0213640 A1 | 9/2007 | Mansour et al. | |
| 2008/0033322 A1* | 2/2008 | Feuer | A61B 5/1076 600/588 |
| 2014/0373367 A1* | 12/2014 | Pinal | B43L 7/005 33/1 N |

* cited by examiner

METHODS AND APPARATUS FOR CONSISTENT AND ACCURATE CERVICAL DILATION READINGS DURING LABOR AND DELIVERY

CROSS-REFERENCE TO RELATED APPLICATIONS

This application claims the benefit of U.S. Provisional Application No. 62/133,897, filed Mar. 16, 2015, which is incorporated herein by reference.

FIELD

The present invention is generally related to practitioners working in labor and delivery of an infant, and more particularly, the present invention discloses methods and apparatus for consistent and accurate cervical dilation readings during labor.

BACKGROUND

Every day many practitioners, such as doctors, nurses, midwives and others, assist in the labor and delivery of infants. One problem that arises is inconsistency of cervical dilation readings or measurements between different practitioners, and inconsistency within cervical dilation measurements by the same practitioner. Because of the length of labor, the same practitioner usually does not follow the entire labor course of a given patient; therefore many practitioners are involved in the management of a laboring patient, leading to discrepancies and/or inconsistencies between cervical exams (especially at shift changes). Each of the practitioners may utilize different methods and techniques to obtain cervical dilation readings or measurements. Sometimes the same practitioner may obtain different readings when checking twice.

Inconsistency of cervical dilation readings may lead to problems managing labor. For example, accurate readings of progress of labor are essential because if the readings are inaccurate:

The actual present stage of labor is unknown.
The length of labor may be affected.
Practitioners may fail to offer necessary treatments.
Practitioners may recommend unnecessary treatments, including:
  Drugs
  Maneuvers
  Surgery Different practitioners use different "metrics" to estimate cervical dilation, but these tactics are not standardized and there is no testing of accuracy or precision of the measurements. Generally, a practitioner will insert two fingers into the vagina and feel the cervix. The practitioner will then estimate, by feel, the magnitude of dilation of the cervix. Therefore, the measurement is subjective. In addition, there is no consistent training provided to student practitioners (MDs/midwives/nurses) to standardize the approach.

Studies have been done to determine accuracy of practitioners at determining cervical dilation. One study was designed to measure precision (variation within and between observers) and accuracy of expert cervical assessment against an objective standard using carefully constructed simulators. No examiner achieved correct assessment in every case tested. The assessment of cervical dilation was exactly right in only 175 of 360 cases (48.6%). (Tuffnel et al, Simulation of cervical changes in labour: reproducibility of expert assessment, 1989).

In another study, polyvinyl chloride pipes 1 to 10 cm in diameter were mounted in cardboard boxes and used to simulate cervical examinations. The boxes were designed so that the examiner had to rely solely on proprioception to determine the inner diameter. In the results, a total of 1574 simulated cervical diameter measurements were obtained from 102 examiners in a two-part study. The overall accuracy for determining the exact diameter was 56.3% and intraobserver variability for a given diameter measurement was 52.1%. (Phelps, Accuracy And Intraobserver Variability Of Simulated Cervical Dilatation Measurements, 1995).

While the above studies used simulators, another study was done to determine accuracy in estimation of cervical dilation during the active phase of labor in vivo and to identify independent predictors of inaccuracy. Examinations were performed on 508 women. The researcher and clinicians agreed on the dilation in 250 instances (49.2%) and differed by 2 cm or more in 56 cases (11.0%). (E J Buchmann the Accuracy of cervical assessment in the active phase of labour, 2007).

As is evident, the practitioners differ about half the time in their measurements of cervical dilation. Inaccuracy and imprecision may negatively impact patient care related to treatment and management decisions based on cervical dilation. "Labour management is based on the assessment of the cervix. Decisions to augment labour or even carry out caesarean section are heavily influenced by the progress of labour, and assessment of progress is based on cervical dilation. Variation between observers is therefore important when care is shared and shift changes." (Tufihel et al, Simulation of cervical changes in labour: reproducibility of expert assessment, 1989).

An incorrect cervical dilation measurement may also increase the risk of the practitioner augmenting labor, which can pose risks to both the mother and the baby. Augmenting labor increases the risk of several complications, including:
Cesarean section.
Fetal heart rate decelerations which indicate decreased oxygen delivery to the fetus.
Post partum hemorrhage.
Blood transfusion and related risks.
Infection.
Uterine rupture.

Tools have been developed or examined to assist the practitioner in determining cervical dilation. Examples of such tools include a translabial 3-dimensional (3D) ultrasonogram, mechanical calipers, electrical displacement transducers clipped to opposite sides of the cervical rim, and a caliper-like cervimeter with leaf spring arms that coil against the outer rim of the cervix for measurement.

Each of these tools was found to be unsatisfactory because they are complex, expensive, inaccurate, increase the risk of infection, may cause patient discomfort, and are difficult to integrate into clinical practice. In addition, they can: distort the cervix (introducing measurement error), cause cervical trauma, and are poorly reproducible. They are also time consuming for the practitioner and require substantial training to develop proficiency. Some protrude from the vagina, interfering with vaginal exams and increasing infection risk.

"The determination of cervical dilatation is necessary in the management of labor. The rate of cervical dilatation is used to define the effectiveness of uterine contractions and the adequacy of labor. Lack of progression of cervical dilatation influences the decision to augment labor or to perform a cesarean section. Therefore it is very important that the estimate of cervical dilatation be reasonably close to the true cervical diameter when there is more than one examiner involved in the management of a laboring patient. The digital examination remains the "gold standard" for evaluation of the cervix in pregnancy; however, it has inherent variability." (Phelps, Accuracy And Intraobserver Variability Of Simulated Cervical Dilatation Measurements, 1995).

Thus there is a need for methods and apparatus for accurate and consistent cervical dilation measurements or readings during labor for practitioners, and between different practitioners with the same patient during labor, that avoid the problems mentioned above.

SUMMARY

The present invention generally provides improved devices, systems, and methods to accurately and precisely determine cervical dilation measurements during labor by standardization of measurements within and between practitioners. It allows for increased accuracy across all levels of training and experience and fills an important gap in practitioners ability to accurately and precisely determine cervical dilation measurements during labor. The present invention does not introduce any discomfort or risk beyond that of a routine digital vaginal examination and it fits into work flow on the labor floor without introduction of new machines or complicated technology that requires advanced training.

In a first aspect, embodiments of the present invention provide a cervical dilation reading apparatus. The apparatus comprises a measuring device having a length with a first end and a second end, a fixed attachment configured to couple with a first finger and fixedly engage the first end of the measuring device, and a slidable attachment configured to couple with a second finger and slidably engage the measuring device along the length between the first and second ends.

In another aspect, embodiments of the present invention provide a method for measuring cervical dilation providing a cervical dilation reading apparatus having a measuring device having a length with a first end and a second end, a fixed attachment configured to couple with a first finger and fixedly engage the first end of the measuring device, and a slidable attachment configured to couple with a second finger and slidably engage the measuring device along the length between the first and second ends. Inserting the first and second fingers into the vaginal introitus and locating the cervix and cervical os, placing the first finger on a first side of the cervical os and extending the second finger away from the first finger to a second side, opposite the first side, of the cervical os, wherein extending the second finger away from the first finger also extends the length of the measuring device between the first and second fingers to a substantially extended state. Removing the first and second fingers and determining a diameter of the cervical os by the length of the measuring device in the substantially extended state between the fixed attachment and slidable attachment.

In many embodiments, the fixed attachment and slidable attachment are incorporated into a glove. The fixed attachment may be positioned at a tip or end of the first finger and the slidable attachment may be positioned at a tip or end of the second finger In many embodiments, the slidable attachment includes a locking mechanism configured to fix or lock a length of the measuring device in a substantially extended state when the slidable attachment is slid or moved away from the fixed attachment. The substantially fixed or locked length of the measuring device may be a cervical dilation measurement. The locking mechanism may be configured to allow sliding or movement of the measuring device in only one direction through the slidable attachment. In some embodiments, the locking mechanism may be configured to allow sliding or movement of the device in a second direction through the slidable attachment when force is applied to the measuring device in a second direction.

In many embodiments, the measuring device includes thin projections or collapsible arrows along the length configured to lay down or collapse as they go through the locking mechanism of the slidable attachment in a first direction when the slidable attachment is slid or moved away from the fixed attachment and then expand after going through the locking mechanism, preventing the measuring device from moving backward in a second direction, thereby locking the measuring device in the substantially extended state.

In many embodiments, the measuring device includes material that, due to friction or pressure, resists movement through an opening of the locking mechanism of the slidable attachment, such that after going through the opening of the locking mechanism, friction or pressure between the measuring device and slidable attachment prevents the measuring device from moving backward in a second direction, thereby locking the measuring device in the substantially extended state.

In many embodiments, the measuring device includes ridges along the length configured to "pop through" an opening of the locking mechanism of the slidable attachment in a first direction when the slidable attachment is slid or moved away from the fixed attachment, the ridges being larger than the opening, such that after going through the locking mechanism, the ridges prevent the measuring device from moving backward in a second direction, thereby locking the measuring device in the substantially extended state.

In many embodiments, the measuring device is configured to engage a ratcheting mechanism for locking the measuring device to the slidable attachment forming the locking mechanism, such that after going through the locking mechanism, the ratcheting mechanism prevents the measuring device from moving backward in a second direction, thereby locking the measuring device in the substantially extended state.

In many embodiments, the measuring device includes measurement markings along the length to measure a cervical dilation measurement. The measurement markings may be in centimeters. In many embodiments, the distance between every other centimeter is colored. In many embodiments, each centimeter is marked with a thick line. In many embodiments, the distance between every other centimeter has radiant color changes, so 0-1 cm is a first color, 1-2 cm is a second color, 2-3 is a third color, 3-4 is a fourth color, and so on with different colors.

BRIEF DESCRIPTION OF THE DRAWINGS

The present embodiments may be understood from the following detailed description when read in conjunction with the accompanying figures. It is emphasized that the various features of the figures are not necessarily to scale. On the contrary, the dimensions of the various features may be arbitrarily expanded or reduced for clarity.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
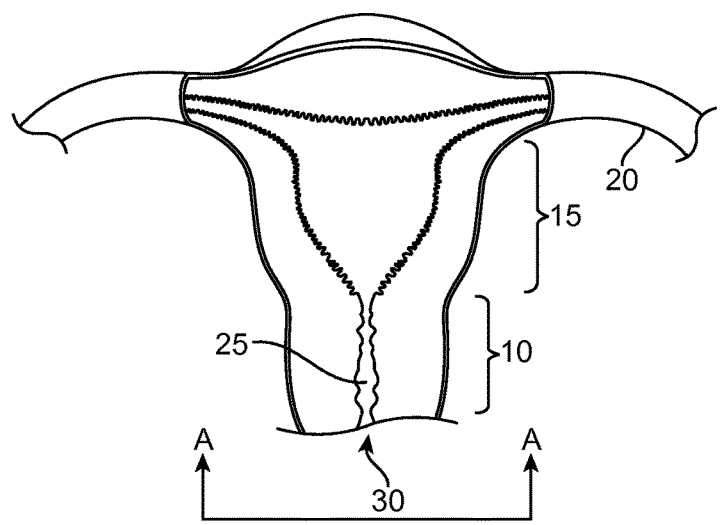
FIG. 1 shows a cross-sectional view of the cervix, uterine body and fallopian tubes, according to the embodiments provided herein.

FIG. 1 shows a cross-sectional view of the cervix 10, uterine body 15 and fallopian tubes 20. The cervix 10 (or neck of the uterus) is the lower, narrow portion of the uterus where it joins with the top end of the vagina. It is cylindrical or conical in shape and protrudes through the upper anterior vaginal wall. The portion projecting into the vagina is referred to as the portio vaginalis 25. The cervix's opening is called the os 30. The size and shape of the os and the cervix vary widely with age, hormonal state, and whether the woman has had a vaginal birth. At labor, the cervix dilates or opens to admit the infant's head.

Cervical Dilation

Figures 2A, 2B:
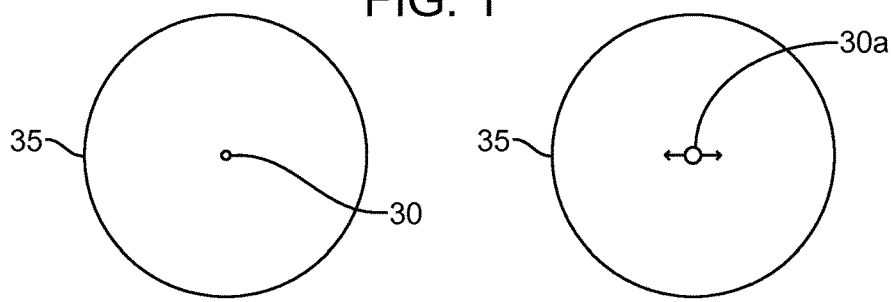
FIGS. 2A-2E show views looking "head-on" at the cervical face (A-A in FIG. 1), according to the embodiments provided herein.

FIGS. 2A-2E show views looking "head-on" at the cervical face 35 (A-A in FIG. 1). For women who are not in labor, the cervix appears to have a small circular dimple 30 (os) at its center. This is a closed cervix. It will not admit a finger. FIG. 2A shows an example of a cervix that is not dilated, so the dilation measurement would be 0 centimeters (cm). FIG. 2B shows an exam example of the first stage of cervical dilation of the cervical os 30a.

Figures 2C, 2D:
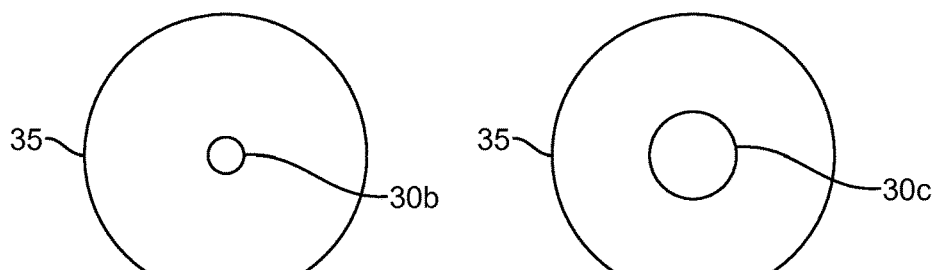

As labor progresses, the cervical os 30b starts opening. In FIG. 2C, the practitioner may be able to insert one finger into the cervical opening, so the dilation measurement might be considered 1 cm for most practitioners. In FIG. 2D, the cervical opening 30c opens more and the practitioner may be able to insert two fingers into the cervical opening, so the dilation measurement might be considered 2 cm.

Beyond 2 cm of dilation, or cervical dilation that will accommodate approximately two fingers for most practitioners, critical differences in cervical measurements between practitioners may emerge. Measurement differences between practitioners may become a critical issue for treatment during labor, as described above in the Background.

Figure 2E:
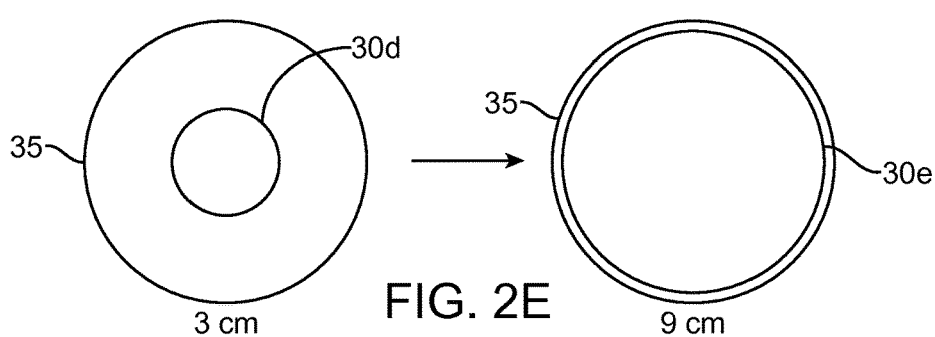

FIG. 2E shows dilation of the cervical opening that has opened between 3 cm 30d (left side) and 9 cm 30e (right side). Between 3 cm and 9 cm, there is no consistent measurement standard that practitioners use. As mentioned previously, measurement tactics are not standardized and there is no testing of accuracy or precision of the measurements.

The ideal method and apparatus for use during labor for measuring cervical dilation may include one or more of the following:

Maximize patient comfort.
No risk of cervical trauma beyond that of a simple digital vaginal examination.
Easily adapted by labor floor practitioners.
Minimally invasive.
Minimize risk of introducing infection.
No expensive machines or technology.
No cumbersome attachments to the patient that may restrict movement or comfort.
Highly reproducible results/readings between practitioners and within the same practitioner (precision).
Accurate readings of cervical dilation.
Fits into current labor room workflow.
Informs treatment and management decisions.
Inexpensive/disposable.
Accurate/Repeatable Measurements The disclosed invention is designed to provide highly reproducible results/readings between practitioners and within the same practitioner.

Figure 3A:
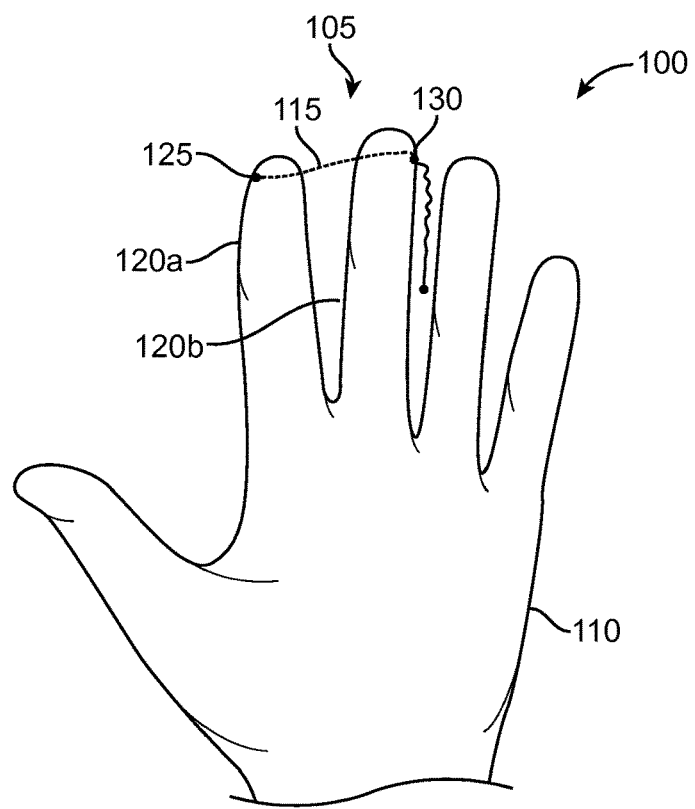
FIG. 3A is an overall view and FIG. 3B is a close-up view showing one embodiment of a cervical dilation reading apparatus incorporating a measuring device as part of a sterile glove to provide accurate and reproducible readings of cervical dilation, according to the embodiments provided herein.
Figure 3B:
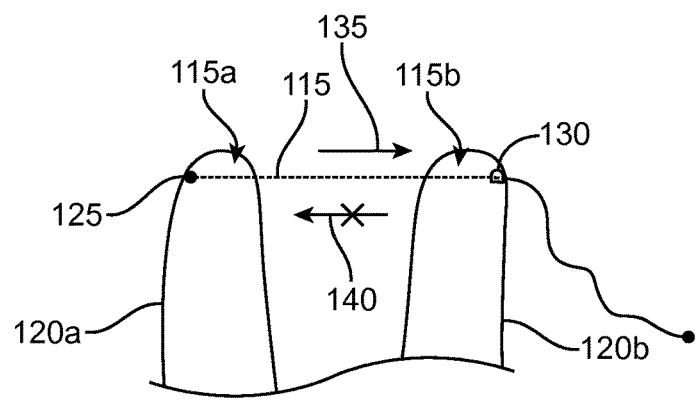

FIG. 3A is an overall view and FIG. 3B is a close-up view showing one embodiment of a cervical dilation reading apparatus 100 incorporating a measuring mechanism 105 as part of a sterile glove 110 to provide accurate and reproducible readings of cervical dilation. In the embodiment shown, the measuring mechanism 105 includes a measuring device 115 spanning between two adjacent fingers 120a, 120b of the glove. In other embodiments, the measuring device 115 may span more than two fingers, span non-adjacent fingers, or be incorporated into the sterile glove by other means. The measuring device 115 has a first end 115a attached to a fixed or stable attachment 125 at a tip or end of the first finger, such as finger 120a and a second end 115b coupled to a slidable attachment 130 at the tip or end of the second finger, such as finger 120b.

Slidable Attachment—

In use, the practitioner would insert the first finger 120a and the second finger 120b into the cervical opening 30. The practitioner would place the first finger 120a on one side of the cervical opening 30 and then move the second finger 120b toward the other side of the cervical opening. The first end 115a of the measuring device 115 is fixed to finger 120a and the second end 115b of the measuring device 115 slides through slidable attachment 130 of the second finger 120b, thereby lengthening the measuring device 115 to obtain the correct dilation measurement. Once to the other side, the practitioner would then withdraw the reading apparatus 100 and measuring device 115 and read the dilation measurement from the second end 115b of the measuring device 115.

Slidable Attachment Locking Mechanism—

In some cases, the measuring mechanism 105 may move or change length as it is being withdrawn after the dilation measurement, so in some embodiments the slidable attachment 130 includes a locking mechanism to fix the length of the measuring device 115 after the dilation measurement.

In the embodiments shown below, the slidable attachment 130 includes a locking mechanism that is designed to allow the measuring device 115 to slide in only one direction 135 to lengthen the measuring device 115 without any back sliding 140 after dilation measurement, such as shown in FIG. 3B. This one-way action allows any practitioner to utilize the reading apparatus 100 and, once the measuring device 115 is locked in place, obtain the same measurement as any other practitioner would obtain with the same or similar device. The locking mechanism allows the measuring mechanism 105 to be withdrawn without the measuring device 115 moving, thereby getting the most consistent results between practitioners and maximizing patient comfort and practicality.

Figure 3C:
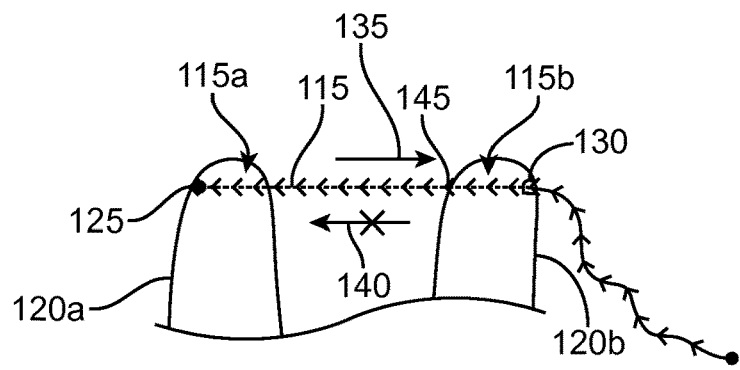
FIGS. 3C-3E show some embodiment examples of locking mechanism for use with a slidable attachment, according to the embodiments provided herein.
Figure 3D:
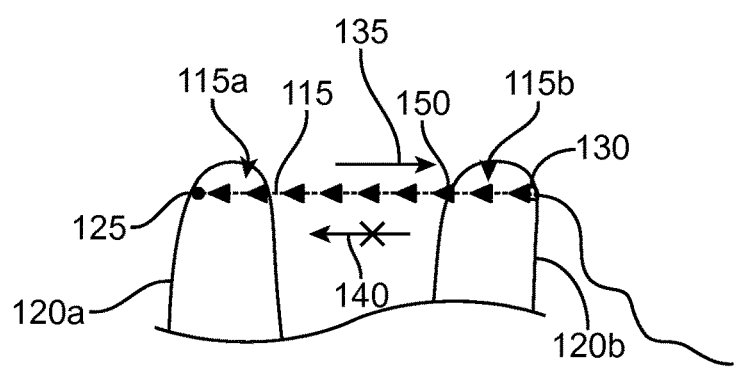
Figure 3E:
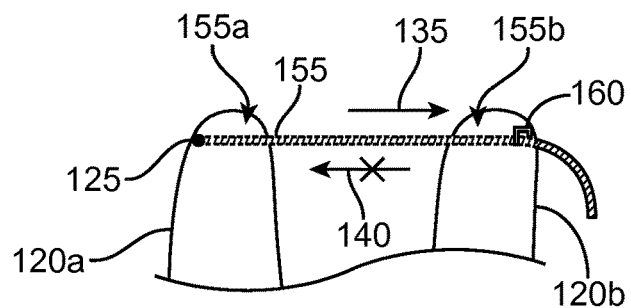

FIGS. 3C-3E show some embodiment examples of a locking mechanism for use with a slidable attachment. FIG. 3C shows one embodiment of a measuring device 115 having thin projections, collapsible arrows, or barbs 145 that compress or collapse as they go through the locking mechanism of the slidable attachment 130 in a first direction 135 when the fingers 120a, 120b are separated. The thin projections or collapsible arrows 145 then expand after going through the locking mechanism, preventing them from moving backward in a second direction 140, thereby locking the measuring device 115 in the substantially extended state after measuring the dilation measurement. This will then lock the measuring device 115 in the correct length for the dilation measurement.

FIG. 3D shows another embodiment of a measuring device 115 having ridges 150 that "pop through" the locking mechanism of slidable attachment 130 in a first direction 135 as the fingers 120a, 120b are separated. Once the ridges 150 "pop through" the locking mechanism, the measuring device 115 can not move backward in a second direction 140, thereby locking the measuring device 115 in the substantially extended state after measuring the dilation measurement. This will then lock the measuring device 115 in the correct length for the dilation measurement.

FIG. 3E shows another embodiment of a measuring device 155 that uses a cable tie or tie-wrap, also known as a hose tie, zap-strap, or zip tie with a ratcheting mechanism 160 for locking the measuring device 155 on the slidable attachment 130. The measuring device 155 slides in a first direction 135 as the fingers 120a, 120b are separated. Once through the ratcheting mechanism 160, the measuring device 155 can't move backward in a second direction 140, thereby locking the measuring device 155 in the substantially extended state after measuring the dilation measurement. This will then lock the measuring device 155 in the correct length for the dilation measurement.

In some embodiments, the measuring device 115 includes material that, due to friction with the slidable attachment 130, resists movement through an opening of the locking mechanism of the slidable attachment 130, such that after going through the opening, friction prevents the measuring device 115 from moving backward in a second direction, thereby locking the measuring device 115 in the substantially extended state.

In some embodiments, the measuring device 115 includes material that, due to pressure with the slidable attachment 130, resists movement through an opening of the locking mechanism of the slidable attachment 130, such that after going through the opening, pressure prevents the measuring device 115 from moving backward in a second direction, thereby locking the measuring device 115 in the substantially extended state.

In some embodiments, the practitioner needs to be able to move fingers around at will while searching for the edges of the cervix without worrying about overshooting the measurement. In this case, the locking mechanism may be configured to allow sliding or movement of the device in a second direction through the slidable attachment when force is applied to the measuring device in a second direction. This allows the practitioner to tighten it back up by pulling on the string.

Measuring Mechanism/String Measurement—

The measuring device 155 of the measuring mechanism 105 is used to measure dilation of the cervical opening as labor progresses and can be made of any pliable material that would be suitable for measurement purposes. In the embodiments shown, the measuring device is a string having markings to measure dilation, preferably in centimeters, but other measurement units may be used. Different measuring mechanisms could be used to make the determination of string length, some examples are described below. If no markings are utilized on the string, the length of the string can be compared to a ruler by the practitioner to determine the length after the measurement is complete.

Figure 4A:
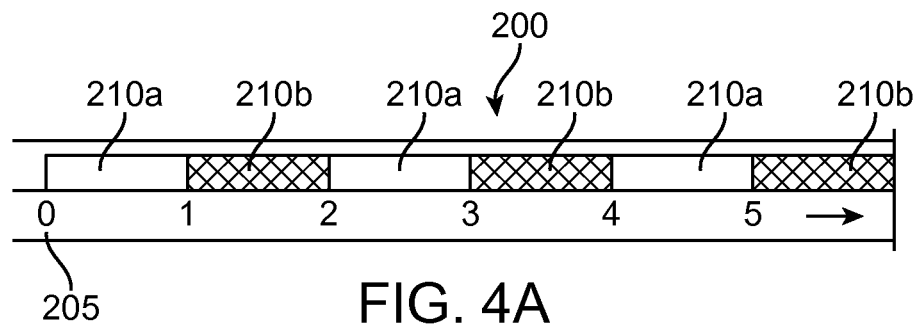
FIGS. 4A-4C show some embodiment examples of a measuring device that have markings on a string to measure the dilation measurement during labor, according to the embodiments provided herein.
Figure 4B:
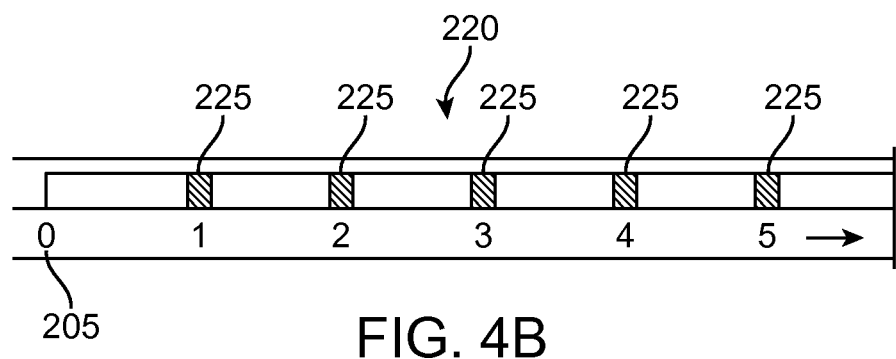
Figure 4C:
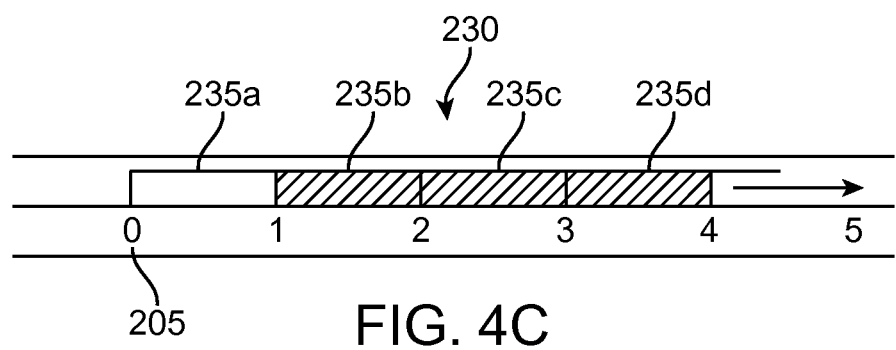

FIGS. 4A-4C show some embodiment examples of measuring devices that have markings to measure the dilation measurement during labor. This system makes it fast and easy, with consistent results, for the practitioners to use the measuring device to measure dilation. While the embodiments below will be described with a string, other suitable materials may be used.

FIG. 4A shows one embodiment of a string 200 with markings in centimeters 205, where the distance between every other centimeter is colored, so 0-1 cm is a first color 210a, 1-2 cm is a second color 210b, and so on, with the colors repeating. Once the practitioner has withdrawn the reading apparatus 100 from the cervical opening, the practitioner then uses the section and/or color on the string 200 to determine the dilation measurement proximate the slidable attachment 130.

FIG. 4B shows another embodiment of a string 220 with markings in centimeters 205, where every centimeter has a thick line 225 that is easy for the practitioner to read (like a ruler). Once the practitioner has withdrawn the reading apparatus 100 from the cervical opening, the practitioner then uses the thick line 225 on the string 220 to determine the dilation measurement proximate the slidable attachment 130.

FIG. 4C shows one embodiment of a string 230 with markings in centimeters 205, where the distance between every other centimeter has radiant color changes, so 0-1 cm is a first color 235a, 1-2 cm is a second color 235b, 2-3 is a third color 235c, 3-4 is a fourth color 235d, and so on with different colors. Once the practitioner has withdrawn the reading apparatus 100 from the cervical opening, the practitioner then uses the color on the string 230 to determine the dilation measurement proximate the slidable attachment 130.

Steps for Use
1. Proper consent is obtained and the patient is appropriately prepared for a digital vaginal examination.
2. Practitioner puts the glove on in a sterile fashion.
3. According to practitioner and patient preference, the practitioner may apply sterile lubricant to fingers to be used in the examination, for example, the pointer (or 2nd finger) and middle (or 3rd finger). This is optional and used routinely in obstetric practice to increase patient comfort with digital vaginal examination. Lubricant has no effect on the device or measurement.
4. Practitioner inserts $2^{nd}$ and $3^{rd}$ fingers into the vaginal introitus. The practitioner finds the cervix and places the $2^{nd}$ finger stationary at the patient's right side of the cervical os (or left side if the practitioner is left-handed). The practitioner extends the $3^{rd}$ finger to the opposite side of the cervical os, extending the string. Care is taken not to stretch, distort or injure the cervix.

5. The practitioner now begins to remove his/her hand, allowing the two fingers to close to prevent patient discomfort.
6. Once the hand is removed, the practitioner carefully extends the $2^{nd}$ and $3^{rd}$ finger without further sliding along the catching mechanism. The practitioner can use the length of the string to determine the diameter of the cervical os.
7. The measurement of the cervical dilation is recorded.
8. The glove/device is disposed of.

The disclosed invention fills an important gap in practitioners ability to accurately and precisely determine cervical dilation measurements during labor.

It provides standardization of measurements within and between practitioners.

It does not introduce any discomfort or risk beyond that of a routine digital vaginal examination.

It fits into work flow on the labor floor without introduction of new machines or complicated technology that requires advanced training.

It allows for increased accuracy across all levels of training and experience.

Currently, no device or technology exists to fill this gap in practitioner's clinical ability/practice.

No device of this nature has ever been described or introduced.

As such, this device presents a novel and important addition to medicine.

While embodiments and applications of this invention have been shown and described, it would be apparent to those skilled in the art that many more modifications than mentioned above are possible without departing from the inventive concepts herein. It is to be understood that the present disclosure is illustrative only and that changes, variations, substitutions, modifications and equivalents will be readily apparent to one skilled in the art and that such may be made without departing from the spirit of the invention as defined by the following claims.

The invention claimed is:

1. A cervical dilation reading apparatus consisting of:
   a measuring device consisting of a pliable string having a length with a first end and a second end, wherein the measuring device includes a plurality of thin projections, collapsible arrows, barbs, or ridges and two or more measurement markings on a length of the measuring device to measure a cervical dilation measurement, wherein the measurement markings are in centimeters, and wherein said measurement markings constitute colored 1 centimeter lengths of the measuring device;
   a fixed attachment configured to couple with a first finger and fixedly engage the first end of the measuring device; and
   a slidable attachment configured to couple only with a distal portion of a second finger and configured to slidably engage the measuring device along the length between the first and second ends such that the measuring device is capable of sliding through the slidable attachment in a first direction when the fixed attachment is moved away from the slidable attachment and in a second direction that is opposite of the first direction;
   wherein the slidable attachment includes a locking mechanism configured to fix a length of the measuring device in an extended state when the slidable attachment is slid or moved away from the fixed attachment in the first direction;
   wherein the locking mechanism is further configured to provide resistance to movement of the measuring device in both the first direction and the second direction;
   wherein the locking mechanism is configured such that said resistance to movement in either the first or second directions may be overcome by application of force to the measuring device in an opposite direction;
   wherein the locking mechanism consists of a passage through the slidable attachment through which the measuring device passes;
   wherein an interior width of the passage is less than a maximum diameter of the measuring device; and
   wherein a length of the measuring device between the slidable attachment and the second end of the measuring device is free and unencumbered.

2. The apparatus according to claim 1, wherein the fixed attachment and slidable attachment are coupled with a glove.

3. The apparatus according to claim 2, wherein the fixed attachment is positioned at a tip of the first finger and the slidable attachment is positioned at a tip of the second finger, wherein the slidable attachment does not extend in a proximal direction beyond a most distal finger joint.

4. The apparatus according to claim 1, wherein the fixed length of the measuring device is a cervical dilation measurement.

5. The apparatus according to claim 1, wherein every other measurement marking is colored with one or two alternating colors.

6. The apparatus according to claim 1, wherein each measurement marking has radiant color changes, so 0-1 cm is a first color, 1-2 cm is a second color, 2-3 is a third color, 3-4 is a fourth color, and so on with different colors.

7. A method for measuring cervical dilation comprising:
   providing a cervical dilation reading apparatus as described in claim 1;
   inserting the first and second fingers into the vaginal introitus;
   locating the cervix and cervical os;
   placing the first finger on a first side of the cervical os;
   extending the second finger away from the first finger to a second side, opposite the first side, of the cervical os, wherein extending the second finger away from the first finger also extends the length of the measuring device between the first and second fingers to an extended state;
   closing the first and second fingers;
   removing the first and second fingers; and
   determining a diameter of the cervical os by the length of the measuring device in the extended state between the fixed attachment and slidable attachment.

* * * * *